United States Patent [19]

Vollhardt

[11] Patent Number: 4,743,432
[45] Date of Patent: May 10, 1988

[54] VERTICAL REACTOR FOR THE GENERATION OF METHANOL

[75] Inventor: Frohmut Vollhardt, Oberhausen, Fed. Rep. of Germany

[73] Assignee: M.A.N. Maschinenfabrik Augsburg-Nürnberg, Fed. Rep. of Germany

[21] Appl. No.: 787,654

[22] Filed: Oct. 16, 1985

[30] Foreign Application Priority Data

Nov. 16, 1984 [DE] Fed. Rep. of Germany ....... 3441917

[51] Int. Cl.$^4$ .............................................. B01J 8/02
[52] U.S. Cl. .................................. 422/196; 422/148; 422/202
[58] Field of Search ............... 422/191, 201, 202, 208, 422/218, 236, 238, 239, 49, 148, 194, 195, 220, 213, 216, 311, 173, 188, 196, 207

[56] References Cited

U.S. PATENT DOCUMENTS

| | | | |
|---|---|---|---|
| 2,045,596 | 6/1936 | Hammell | 422/49 |
| 2,512,586 | 6/1950 | Stengel | 422/148 X |
| 3,477,828 | 11/1969 | Schulze et al. | 422/148 |
| 3,784,361 | 1/1974 | Kubec et al. | 422/49 |
| 4,101,281 | 7/1978 | Pagani | 422/148 |
| 4,166,834 | 9/1979 | Reed et al. | 422/148 |
| 4,180,543 | 12/1979 | Ward | 422/191 X |
| 4,321,234 | 3/1982 | Ohsaki et al. | 422/218 X |
| 4,335,076 | 6/1982 | McFarland | 422/173 X |
| 4,359,448 | 11/1982 | Schuurman et al. | 422/49 X |
| 4,372,920 | 2/1983 | Zardi | 422/192 X |
| 4,420,462 | 12/1983 | Clyde | 422/201 |
| 4,559,207 | 12/1985 | Hiller et al. | 422/201 X |
| 4,584,180 | 4/1986 | Ostrov | 422/207 |
| 4,632,587 | 12/1986 | Vollhardt | 422/202 |

FOREIGN PATENT DOCUMENTS

| | | |
|---|---|---|
| 3332049 | 3/1985 | Fed. Rep. of Germany . |
| 1204634 | 9/1970 | United Kingdom . |
| 2060426 | 5/1981 | United Kingdom . |

*Primary Examiner*—Barry S. Richman
*Assistant Examiner*—Jill Johnston
*Attorney, Agent, or Firm*—McGlew and Tuttle

[57] ABSTRACT

An upright reactor for the generation of methanol comprises a cylindrical housing closed by a removable hood, where several catalyst beds, arranged one over the other and each carried by a detachable gas-permeable bottom or net, are surrounded by a cylindrical jacket of finned tubes into which open the ends of the exchanger tubes traversing the catalyst bed. According to the invention, horizontal gas-impermeable partitions are arranged below the gas-permeable bottoms or nets of the second lowest and of the next highest catalyst beds at the level of inflow or outflow openings for the gas.

8 Claims, 1 Drawing Sheet

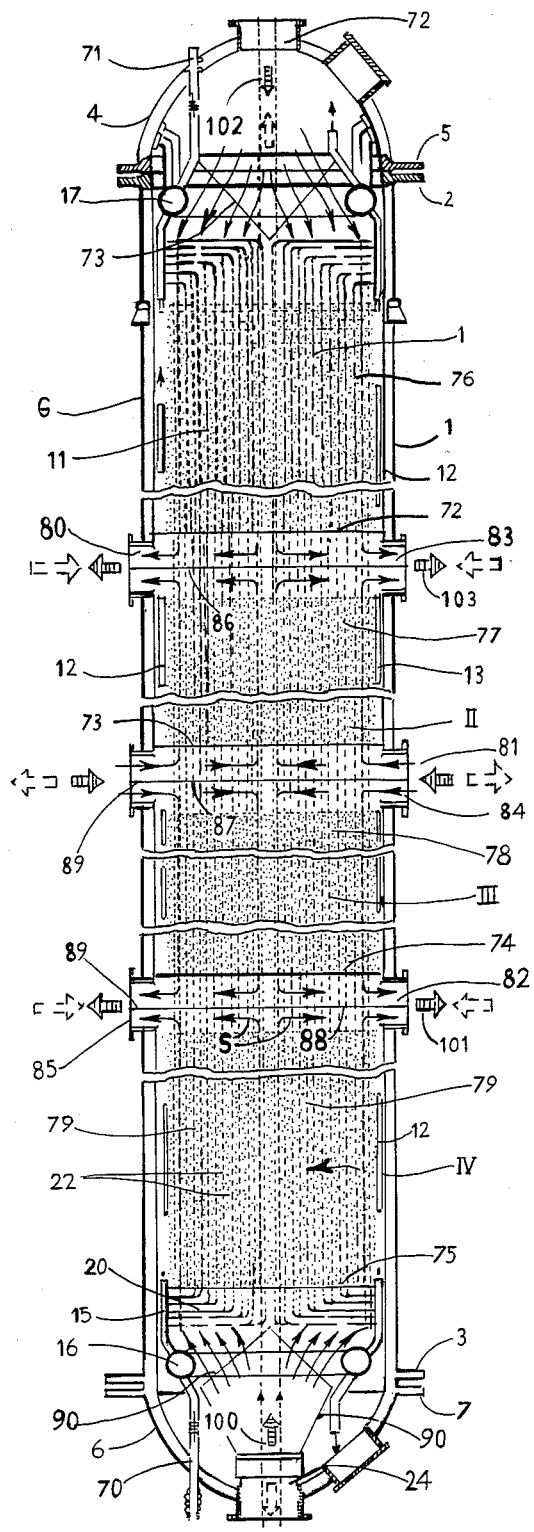

VERTICAL REACTOR FOR THE GENERATION OF METHANOL

FIELD AND BACKGROUND OF THE INVENTION

This invention relates in general to reactor vessel construction and in particular to a new and useful upright methanol generator reactor having a plurality of vertically arranged catalyst beds.

German patent application P No. 33 32 049.7-42 provides in one form of realization that the housing of the reactor is closed off by an upper removable hood and the catalyst bed is surrounded by a cylindrical jacket of finned tubes, open at the top, closed by a detachable bottom or net at the bottom, where several catalyst beds, arranged one over the other and each carried by a detachable, gas-permeable bottom or net and are surrounded by a cylindrical jacket of finned tubes.

SUMMARY OF THE INVENTION

This application is an improvement over the reactor construction set forth and described in the application Ser. No. 637,759 filed Aug. 6, 1984 the disclosure of which is incorporated herein by reference and now allowed and filed by the applicant of the present case.

The invention provides an improved vertical reactor in which the heat content of the gas is utilized still more effectively with simple means.

In accordance with the invention an upright methanol generator reactor comprises an exterior cylindrical pressure jacket with a cylindrical heat exchanger arranged within and having an outer wall of tubes spaced inwardly from the interior of the cylindrical pressure jacket with the space between the tubes filled with catalyst so as to form a plurality of vertically arranged catalyst beds each having a gas-permeable bottom which is below each bed and supports it. The substantially horizontal partition is arranged at a spaced location below each of the bottoms in respect to the catalyst bed which is above the lowermost one and fluid flow openings are disposed in the cylindrical jacket at the level of the partitions. The partitions are advantageously arranged at mid-height of the inflow or outflow openings of the vessel. The cooling gas medium is circulated through the tubes of the heat exchanger and a gas is directed for flow upwardly through the lowermost catalyst bed and then successively out of an opening below the partition and into the opening above the partition for flow through successive vertically arranged catalyst beds. The partitions advantageously include projections which extend into nipples or connections for the fluid flow openings and divide the openings vertically into a plurality of passages. The gas streams traversing the catalyst flow beds advantageously have the same flow direction into and out of the openings both above and below the partitions so that the connecting lines to the nipples can feed the gases in the same direction to more than one flow passage.

The reactor according to the invention offers the advantage, while observing the task and the advantages of the previous similar devices, of obtaining an increased heat transfer from the gases and from the catalyst substance contacted by them to the cooling medium, so that a high performance of the heat exchanger is achieved.

Accordingly it is an object of the invention to provide an improved upright methanol generator reactor which includes a plurality of catalyst beds formed by catalyst material between the tubes of the cylindrical heat exchanger arranged within a cylindrical housing in which each vertically arranged catalyst bed is supported by a net or bottom and the flow for the fluids is effected through openings having nipples which are divided by partitions arranged between adjacent reactor beds spaced from the bottom of the net supporting the beds.

A further object of the invention is to provide an upright methanol generator which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the drawings:

The only FIGURE of the drawings is an axial sectional view of an upright methanol generator reactor constructed in accordance with the invention.

DESCRIPTION OF THE PREFERRED EMBODIMENT

Referring to the drawing in particular, the invention embodied therein comprises an upright methanol generator reactor which includes a cylindrical pressure jacket 1 with a cylindrical heat exchanger 11 having an outer wall of fluid tubes or finned tubes 12 which are arranged within the heat exchanger 11. The catalyst bed is arranged between the tubes and in the reactor vessel shown they form four separate superjacent beds 76, 77, 78, and 79. Each of the beds has a gas-permeable bottom 72, 73, 74, 75 through which the tubes 12 of the heat exchanger 11 pass and which supports an associated catalyst bed.

In accordance with the invention, a substantially horizontal partition 86, 87, 88 is arranged at a spaced location below each of the bottoms 72, 73, 74 which are above the lowermost bottom 75. In addition, a fluid flow opening 83, 84, 85 is provided in the pressure jacket 1 at the level of the partitions 86, 87 and 88.

The housing G of the reactor comprises an outer cylindrical pressure jacket 1, which extends from the upper section to the lower section of the reactor and presents a flange 2, 3 at its upper and lower edges. Upwardly the housing G is closed by a hood 4, whose flange 5 is connected with the flange 2 of the cylindrical pressure jacket 1, while the bottom 6 of housing G is connected by its flange 7 with flange 3 of the pressure jacket 1.

Preferably the pressure jacekt 1 is lined with an insulation layer which extends from the joint between flanges 2 and 5 to the joint of the flanges 3 and 7. The design of the pressure jacket 1 and of the hood 4 and bottom 6 with their linings is chosen so that hood 4 can be removed from the pressure jacket 1 without difficulties. The same applies, if this is necessary, to the bottom 6.

The insulating layer which lines the cylindrical jacket 1 surrounds a cylindrical heat exchanger 11. The heat exchanger 11 comprises a cylindrical jacket 13 closed at its circumference and formed by finned tubes 12. The upper and lower ends of the finned tubes 12 of jacket 13 open into a thicker tube section 14,15, these tube sections leading into a lower manifold ring conduit 16 and into an upper collecting ring conduit 17. The cooling medium for the heat exchanger 11 is supplied to the ring conduit 16 via one or more tubes 70 traversing the bottom 6 and its lining, while the heated cooling medium is drawn off from the collecting ring conduit 17 via one or more tubes 71 which are passed through hood 4.

Into the thickened tube sections 14, 15 of the finned tubes 12 of the cylindrical heat exchanger jacket 13 there open tube ends 20, 21, bent into horizontal planes, of the vertical exchanger tubes 22 of the heat exchanger 11 extending parallel to the longitudinal axis of the reactor, so that a uniform exchanger body comprising a finned tube jacket and an inner exchanger tube nest is formed.

In the illustrated example, the interior of the reactor is subdivided into four spaces I,II,III,IV, one above the other, which jointly are surrounded by the finned tube jacket 13 and traversed by the exchanger tubes 22. The lower end of each of these four spaces has a horizontal bottom or screen or net 72, 73,74, 75 extending over the entire clear cross-section of the finned tube jacket 13, which net is easily detachable from its attachment and is gas-permeable, yet is able to carry the catalyst bed 76,77,78,79. Above each of the three lower spaces II-,III, IV, openings 80, 81, 82 are provided in the finned tube jacket 13 and in the pressure jacket 1 of housing G, which openings connect with outwardly directed tube nipples 83,84,85.

At the level of each of the openings 80, 81, 82, a gas-permeable horizontal partition 86,87,88 is arranged, which is situated at mid-height of the clear cross section of the openings 80, 81 82. The partitions 80, 81 and 82 also extend over the cross section of the finned tube jacket, and preferably are provided with portions 89 extending through the nipples.

The bottom 6 has a central gas feed line 24 with a conical distributor 90. The cooled gas of space IV impinges on the partition 88 from below, the latter being traversed by the exchanger tubes 22, as is also the catalyst net 74 thereabove. The gas of space IV is conducted in the direction of the arrows S through the openings 82 and the nipples 85.

To the same nipple 85 is supplied the cooled gas from space III, which impinges on the top side of partition 88 and is deflected outwardly. This partial gas stream goes via the nipples 84 in space III, as does also the partial gas stream for space II, the two spaces II and III being separated by the partition 87 traversed by the tubes 22. The catalyst bed of space II likewise surrounds the tubes 22 which protrude through net 73 of this space.

The flow conditions of partitions 88 correspond to those of partition 86 below space I, to which the gas is supplied through the central feed line 72 via the conical distributor 90.

The flow direction of the gas is illustrated in the drawing by arrows in solid lines. Thus the gas enters the reactor in the direction of arrow 100 through line 24, in order to flow in co-directional flow with the cooling medium in tubes 12 and 22 through the space IV equipped with catalyst substance, and to leave this space in the direction of the arrows 101. The same applies to space I, into which the gas is introduced in the direction of arrow 102, which traverses this space in counter-flow to the cooling medium in the tubes 12 and 22 and leaves the reactor in the direction of the arrows 103. For the spaces II and III the same flow conditions prevail. They may also be reversed, as is indicated by the arrows shown in broken lines. Then there occurs in the spaces II and IV, instead of a co-directional flow of gas and cooling medium, a counter-flow and in the spaces I and III, instead of a counter-flow of these media, a co-directional flow. Also other flow combinations are possible.

While a specific embodiment of the invention has been shown and described in detail to illustrate the application of the principles of the invention, it will be understood that the invention may be embodied otherwise without departing from such principles.

What is claimed is:

1. An upright methanol generator reactor, comprising an exterior cylindrical jacket, a cylindrical heat exchanger having an outer wall of tubes arranged within said pressure jacekt, a plurality of separate super-jacket catalyst beds in said heat exchanger within said outer wall of tubes, a plurality of gas-permeable bottoms, including a lowermost bottom, respective ones of said bottoms being located below and supporting respective catalyst beds, a substantially horizontal gas-impermeable partition arranged spaced from and below each of the bottoms except the lowermost bottom, dividing the interior into separate gas flow compartments surrounding each bed and not in fluid communication with each other and fluid inflow and outflow openings extending through the jacket and communicating with the respective adjacent compartments at locations adjacent each partition.

2. A reactor according to claim 1, wherein said partitions are coextensive with the dimension of said heat exchanger.

3. A reactor according to claim 1, including a bottom member closing said lower end of said cylindrical pressure jacket and a gas inlet opening connected into said bottom near the lower end of the bottommost catalyst bed and including a feed line extending through said bottom connected to said heat exchanger for circulating a heat exchange fluid therethrough.

4. A reactor according to claim 1 further comprising nipples forming said openings wherein said partitions extend through said nipples, said nipples forming connections for inflow and outflow of fluids.

5. A reactor according to claim 1 in which the heat exchanger includes a nest of heat exchanger tubes located within the outer wall of tubes and which traverse all the catalyst beds and have upper and lower ends which open into the tubes of the outer wall of tubes at locations above an uppermost and below a lowermost catalyst bed, respectively.

6. A reactor according to claim 1, further comprising nipples forming said openings and wherein said nipples are arranged in said pressure jacket for inflow and outflow of fluids, said partitions being arranged mid-way between the cross dimension of said openings.

7. A reactor according to claim 1, further comprising nipples forming each of said openings, wherein said nipples are connected to said partitions so that fluid from the nipples flows into adjacent catalyst beds above and below the partitions in the same direction.

8. An upright methanol generator comprising: an exterior cylindrical housing; a removable hood closing said cylindrical housing; a plurality of separate catalyst beds positioned within said cylindrical housing; heat exchanger tubes traversing each of said separate superjacent catalyst beds; a plurality of detachable gas-permeable screens; respective ones of said screens carrying respective catalyst beds and being detachably connected to said cylindrical housing; a plurality of substantially horizontal, gas-impermeable partitions, respective ones of said partitions being arranged to extend horizontally across the housing below respective ones of said gas-permeable screens except a lowermost screen thereby to separate the catalyst beds from each other in respective gas-tight compartments; fluid inflow and outflow openings being provided in the cylindrical housing at locations adjacent and above, and adjacent and below, each partition for admitting and removing fluid from adjacent compartments.

* * * * *